United States Patent
Wagener

(10) Patent No.: US 8,066,694 B2
(45) Date of Patent: Nov. 29, 2011

(54) HOMEOSTATIC INSULIN PUMP

(76) Inventor: Robert Joseph Wagener, Liverpool (GB)

( * ) Notice: Subject to any disclaimer, the term of this patent is extended or adjusted under 35 U.S.C. 154(b) by 32 days.

(21) Appl. No.: 12/267,989

(22) Filed: Nov. 10, 2008

(65) Prior Publication Data

US 2009/0137957 A1    May 28, 2009

(30) Foreign Application Priority Data

Nov. 27, 2007 (GB) .................................. 0723165.7

(51) Int. Cl.
*A61K 9/22* (2006.01)
(52) U.S. Cl. ..................................................... 604/890.1
(58) Field of Classification Search ............... 604/892.1, 604/890.1, 891.1, 65–67; 417/412; 600/309, 600/310, 341
See application file for complete search history.

(56) References Cited

U.S. PATENT DOCUMENTS

| | | | | |
|---|---|---|---|---|
| 4,538,616 A | * | 9/1985 | Rogoff | 600/365 |
| 4,627,850 A | * | 12/1986 | Deters et al. | 604/892.1 |
| 5,062,841 A | * | 11/1991 | Siegel | 604/891.1 |
| 5,995,860 A | * | 11/1999 | Sun et al. | 600/341 |
| 6,203,291 B1 | * | 3/2001 | Stemme et al. | 417/413.3 |
| 6,632,217 B2 | * | 10/2003 | Harper et al. | 604/892.1 |
| 7,011,507 B2 | * | 3/2006 | Seto et al. | 417/412 |
| 7,476,224 B2 | * | 1/2009 | Petrakis | 604/890.1 |
| 2002/0123789 A1 | * | 9/2002 | Francis et al. | 623/1.13 |
| 2002/0123793 A1 | * | 9/2002 | Schaldach et al. | 623/1.15 |
| 2005/0247558 A1 | * | 11/2005 | Anex et al. | 204/275.1 |
| 2005/0261561 A1 | * | 11/2005 | Jones et al. | 600/315 |
| 2008/0029393 A1 | * | 2/2008 | Krumme | 204/600 |
| 2008/0147105 A1 | * | 6/2008 | Wilson et al. | 606/167 |

* cited by examiner

*Primary Examiner* — Christopher D Koharski

(57) ABSTRACT

A permanently implanted insulin pump or combined insulin and glucagon pumps, controlled by a valve that expands and contracts due to osmosis as a result of changes in the blood sugar level. The valve is constructed from tissues harvested or grown from the patient's body tissues to prevent rejection, infection or thrombosis. It operates the pump(s) though a blood vessel via a magnetic strip within the valve tissue and a reed switch located outside the blood vessel. The pump battery is recharged by electromagnetic induction in response to low battery warnings. Glucagon and/or insulin are refilled in response to low-level warning indicators, using self-sealing septa located near to the surface of the skin.

2 Claims, 2 Drawing Sheets

HOMEOSTATIC INSULIN PUMP

CROSS-REFERENCE TO RELATED APPLICATIONS

Figure 1:
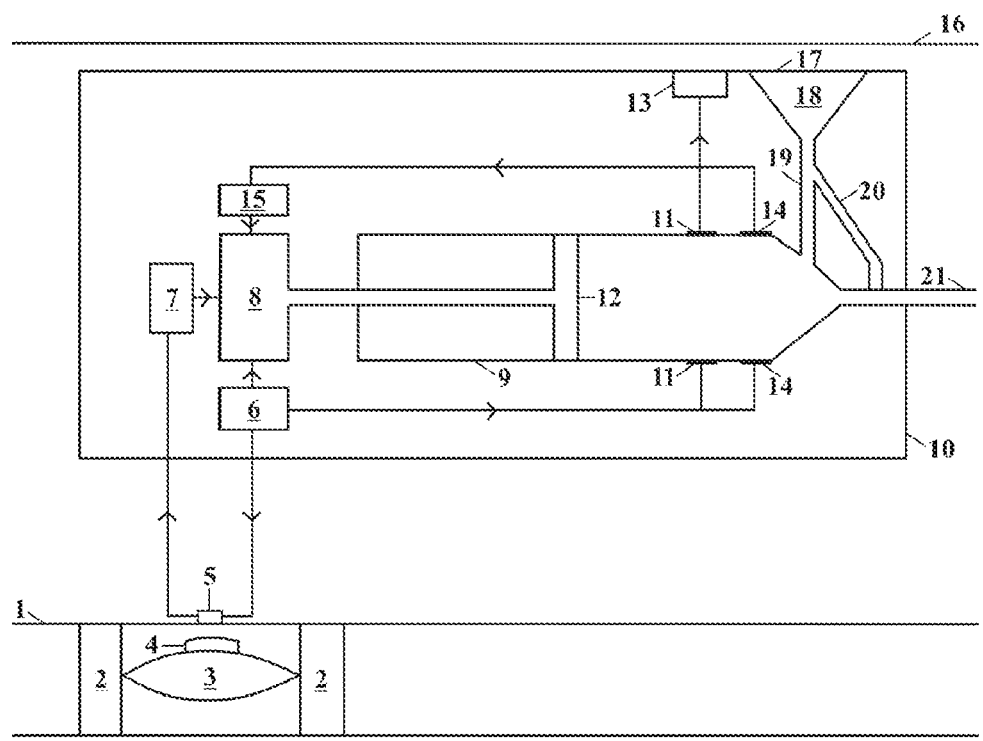

The claims and specification set out below are contained in UK Patent Application number GB0723165.7, which was lodged by the applicant on 27 Nov. 2007. This has a priority date of 27 Nov. 2008 and was published on 6 Aug. 2008 under reference GB 2 446 247 A.

STATEMENT REGARDING FEDERALLY SPONSORED RESEARCH/DEVELOPMENT

Not applicable.

REFERENCE TO SEQUENCE LISTING, A TABLE, OR A COMPUTER PROGRAM LISTING COMPACT DISK APPENDIX

Not applicable.

BACKGROUND OF THE INVENTION

This invention is a medical device principally for the treatment of insulin dependent diabetes (IDDM).

IDDM is an autoimmune disease of the pancreas, which results in the destruction of the Islets of Langerhans (IL). The IL contains two main types of endocrine cells: alpha cells which produce glucagon and beta cells which produce insulin. These antagonistic hormones increase and lower the blood sugar level (BSL) respectively, thereby keeping the BSL within the optimum range of 4 to 7 mmols per liter.

IDDM is generally treated by daily injections of insulin. As this involves the release of predetermined amounts of insulin into the bloodstream, however, the amount of carbohydrate (CHO) and exercise have to be carefully balanced against this to avoid the BSL going too low (hypoglycaemia) or too high (hyperglycaemia).

To maintain a reasonable balance many diabetics have to take several injections and blood tests a day. Even with close monitoring, however, hypoglycaemic episodes ('hypos') are virtually impossible to avoid altogether, and these are particularly dangerous during sleep, as they can quickly lead to unconsciousness or even coma.

If a diabetic's BSL is particularly erratic, an insulin pump may be used instead of traditional injections to provide a steadier release of insulin into the bloodstream. Some of the latest insulin pumps also employ a glucose sensor, which monitors the BSL to determine when and how much insulin should be released. The sensor works by detecting changes in the level of glucose in the interstitial fluid found between the body's cells (IFSL), and then feeding this information to a microprocessor.

One difficulty with existing insulin pumps is that they are situated outside the body, to allow the battery to be recharged and insulin and sensor parts to be replaced. As a result, there is a risk of infection at the insertion sites of the pump and the glucose sensor. There is also a risk that parts of the pump may become detached during sleep, and restless nights are not uncommon, particularly when there are problems with a diabetic's BSL. In addition, it may not be practical to keep the pump on all of the times during the day, for example when washing, swimming, during intimacy, or when taking part in certain sports.

The main problem with insulin pumps that employ glucose sensors is the inevitable delay between changes in the BSL and the IFSL. To compensate for this, the glucose sensor is controlled by a complicated computer programme, which requires data to be input regularly regarding BSL readings and the amount of exercise and CHO taken. Even with these safeguards, however, it is impossible to rule out hypos altogether, which may be acerbated if the pump continues to deliver insulin when the BSL is already dangerously low.

One final problem with pumps is something known as ketoacidosis, a potentially dangerous condition that can arise as a result of hyperglycaemia. It is known that the risk of ketoacidosis is higher with insulin pumps, as they cannot use longer-acting insulins, which provide some protection against this condition.

These problems with the conventional treatments of IDDM have led researchers to consider creating beta cells from a person's T cells and then implanting them in the patient's body. The new beta cells would then secrete insulin in response to changes in the BSL, removing the need for injections or insulin pumps altogether.

To date, techniques for growing large numbers of beta cells are still at a relatively early stage. In addition, as IDDM is an autoimmune disease, there is a high risk that the diabetic's immune system would destroy cells that were identical to the original beta cells. As a result, the implanted cells would have to be protected with a durable coating, which contained microscopic pores that were large enough to let insulin out but small enough to prevent the body's defence systems from entering. Although some protective coatings have been developed, these are also still some way from being perfected.

As with U.S. Pat. No. 4,538,616 of 3 Sep. 1985, this invention employs the principle of osmosis to drive the sensor mechanism. The former device failed, however, due to problems associated with placing a foreign body in the bloodstream, which were highlighted in International Patent WO 98/28605 of 2 Jul. 1998.

U.S. Pat. No. 4,538,616 also contemplated the use of a membrane that was impermeable to other solutes that affect the osmotic pressure of the blood, in particular sodium chloride and sodium lactate. As a result, the device could be adversely affected by changes in osmotic pressure caused by variations in these solutes.

Since U.S. Pat. No. 4,538,616, osmotic devices to control blood sugar level have been designed for use outside the blood stream. International Patent WO 98/28605 of 2 Jul. 1998, therefore, involved an osmotic transducer solely for use in the body tissues. It also does not overcome the problems created by other substances that can affect osmotic pressure, in particular sodium lactate. The device cannot therefore be used when lactic acid rises, e.g. during hard exercise (page 17, line 25).

International Patent WO 91/04704 A of 18 Apr. 1991 suggests an alternative mechanism for measuring osmolality, which would isolate changes in osmotic pressure that were caused by glucose alone. However, this sensing device is made of synthetic substances, and is therefore only suitable for use in the body tissues ('interstitial regions'), as opposed to the bloodstream.

International Patent WO 03/061475 A is very similar to International Patent number WO 91/04704 A, but uses a more sophisticated arrangement of valve chambers to minimise the effects of bio-fouling (page 3, lines 11-13). Once again, therefore, it could not be used in the bloodstream for any length of time.

BRIEF SUMMARY OF THE INVENTION

This invention overcomes the problem of bio-compatibility by employing a valve constructed from the patient's own body tissues. It also overcomes the problems of interference from other blood solutes, by employing a valve membrane tissue that is impermeable to glucose but permeable to the other main solutes that could affect the blood's osmotic pressure.

BRIEF DESCRIPTION ON THE SEVERAL VIEWS OF THE DRAWINGS

FIG. 1

This shows a simple insulin-only pump system, together with the valve and its position in the blood vessel.

FIG. 2

This is a side view of the blood vessel shown in FIG. 1. It illustrates how the flow of blood is able to pass freely around the supports and the valve.

Figure 3:
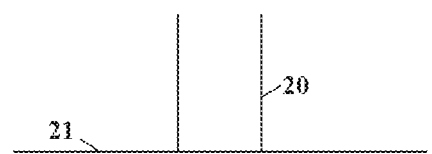
Figure 4:
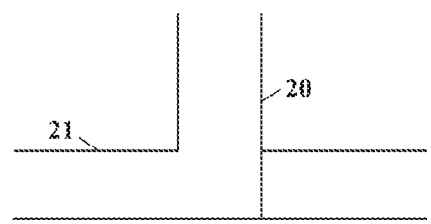
Figure 5:
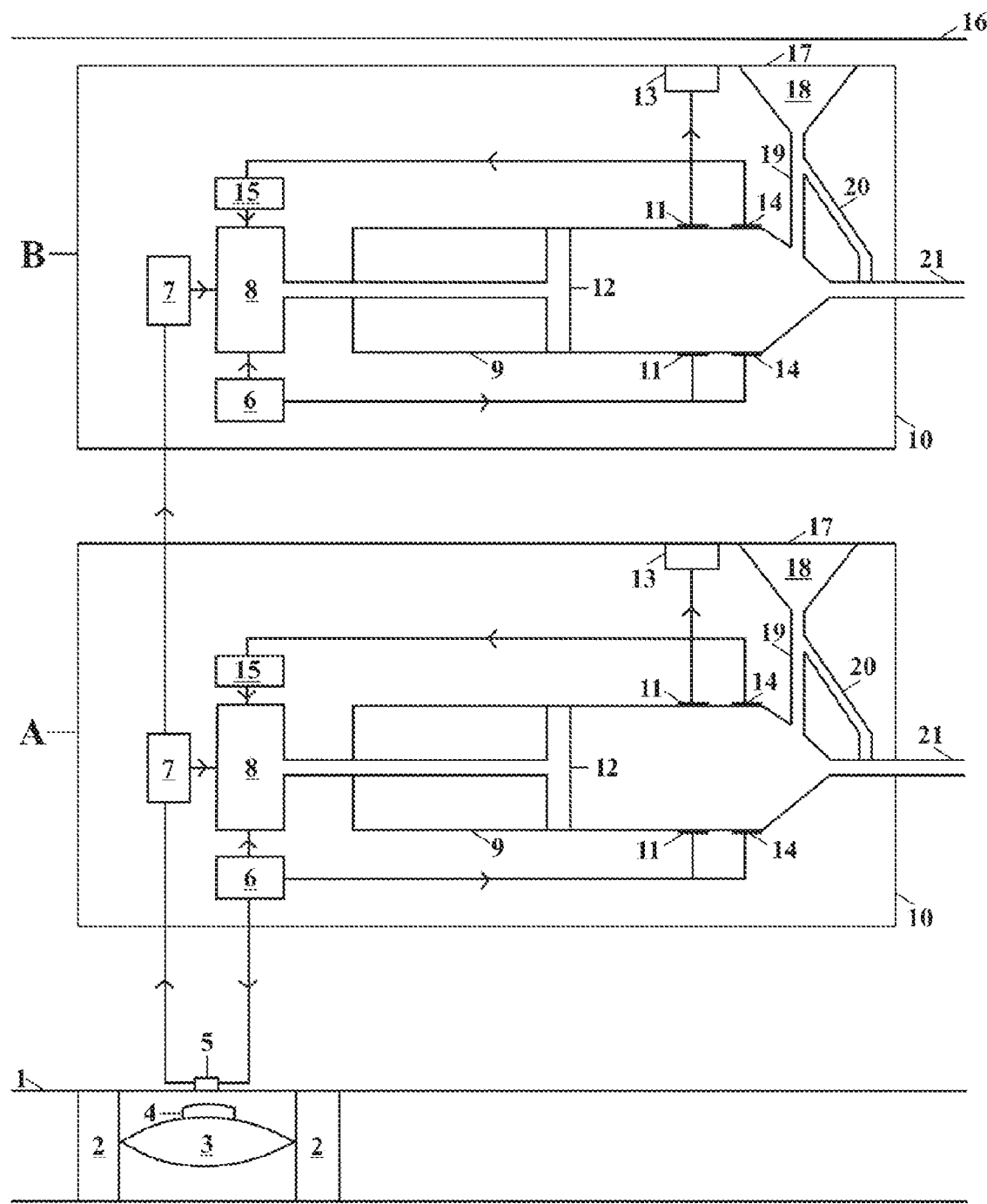

FIGS. 3 and 4

These are close-up views of the end of the refilling tube in FIG. 1. The diagrams show the end of the tube before and during the refilling process to illustrate how the tube distends in FIG. 4. to prevent insulin from escaping.

FIG. 5

This shows the more complicated arrangement involving two pumps, which secrete insulin and glucagon alternately.

DETAILED DESCRIPTION OF THE INVENTION

This invention relates to an implantable insulin pump that controls the BSL homeostatically, thereby mimicking the way in which a healthy pancreas works.

In its simplest form this is achieved this by placing a small valve in the bloodstream and linking this to an insulin pump located inside the body. The valve contains a semi-permeable membrane, which enables it to monitor changes in the BSL by means of osmosis. When the BSL falls below a certain level, the valve expands and switches off the insulin pump. When the BSL rises again, the valve shrinks and the unit begins pumping insulin again.

The valve is made from the patient's own body tissues, thereby removing the risk of rejection and infection. As the pump is implanted in the body permanently, the battery has to be recharged remotely by means of electromagnetic induction. The technology to do this has existed since the beginning of the last century, but recent developments mean that batteries can now be recharged in this way at a distance of up to several feet.

The batteries provide audible and vibrating low battery warning signals. They also activate a similar alarm when the insulin level is low. The insulin is then replaced via a needle, which is inserted through the skin and a self-sealing septum in the insulin pump.

In the more complicated version, finer control of the BSL is achieved by employing two pumps: one secreting insulin and the other, glucagon. The two pumps function in basically the same way. However, when the insulin pump is switched off by the osmotic valve, this also activates the glucagon pump, thereby raising the blood sugar level more quickly. When the BSL reaches a safe level, the insulin pump is switched on again, and this simultaneously deactivates the glucagon pump.

The only difference between the two-pump model and a healthy pancreas is that the latter secretes insulin and glucagon directly into the blood stream, whereas the pump delivers the hormones into the subcutaneous fat. With the pump, therefore, there would be a 10-15 minute delay before the insulin or glucagon reached the bloodstream. As this delay factor is fairly constant, however, it could easily be factored into the calibration of the system at the time of installation (see page 4, paragraph 3).

The following describes in detail the two types of device outlined above, namely the insulin pump and the combined insulin and glucagon pumps. The figures to which the following refer are not drawn to scale and are diagrammatic rather than representational in nature.

FIG. 1 to 4

The sensor device is located inside a vein 1, where it would not be adversely affected by the higher pressures and faster blood flows that exist within arteries. It comprises two supports 2, which hold a valve 3 in place and shield the valve from the effects of blood flow in the vein. To provide further protection for the valve, the supports could be more substantial and perhaps even take the form of a box with apertures in it to allow blood to flow in and out.

Figure 2:
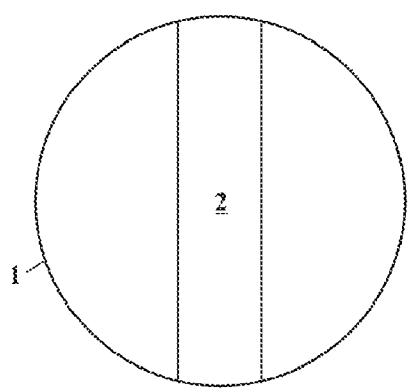

As indicated by FIG. 2, the supports 2 and valve 3 would be narrow enough to permit blood to flow around them. Normal blood supply would not therefore be compromised by the presence of the valve.

In view of its size, construction of the valve would be the most difficult part of the procedure. This could be done, however, using microsurgery techniques and perhaps by removing and then replacing the designated section of the vein.

In the foreseeable future, it may be possible to grow the valve using T cells from that person's own body cells. An artificial blood vessel could also be grown from T cells and then be connected to and from a natural vein. The advantage of this would be that the artificial blood vessel could be designed to have a larger diameter than a normal vein, thereby enabling it to accommodate the valve more easily.

As regards the construction of the supports, these would have to be made of a strong naturally occurring tissue that would not break or wear down in the blood stream. One suitable candidate might be fibrocartilage. Not only does this have great elasticity and tensile strength, it is also generally avascular and does not therefore require a separate blood supply.

The valve is a semi-permeable membrane containing a solution with a glucose concentration set at a safe level above the normal fasting BSL of 4.0 mmols per litre. The optimum concentration of glucose in the valve needs to be calculated to establish the ideal point at which the insulin pump is deactivated. This would require a safe margin for error, as insulin from the pump would continue to lower the BSL some time after it had been secreted.

One possible source for the semi-permeable membrane of the valve might be tissue from the peritoneum. This is impermeable to glucose, but permeable to water and salts. It would therefore allow the passage of water by osmosis, without being affected by changes in sodium chloride or sodium lactate.

Variations in salt levels would also not adversely affect the valve, because, unlike glucose, the body's osmoregulation system is very sensitive to changes in the level of salt in the bloodstream. The body quickly responds to salt level changes by altering the rate of water re-absorption by the kidneys, which enables it to keep plasma osmolality within a narrow range of 280-295 mosmol/kg.

The supports and valve would have to be harvested from mature tissue, so that they did not continue to grow in situ. The supports could be stitched to the vein and the valve via holes in the supports. Once connected, these would knit together to form a permanently sealed connection.

When the BSL of the diabetic falls the osmotic pressure of the blood falls, and water molecules pass into the valve as a result of osmosis. This then causes the valve to expand until it brings together the magnetic strip 4 and a reed switch 5. This completes a circuit, which deactivates the insulin pump in the manner described below.

The reed switch would be permanently stitched to the outside of the blood vessel to ensure it did not become detached. As a further measure, two weak magnets of the same polarity as the strip 4 could be placed alongside and on either side of the reed switch, opposite 4. This would prevent 4 and 5 from being pushed together inadvertently, e.g. by increases in the blood flow.

To prevent the strip 4 from coming into contact with the bloodstream, it would be covered by some kind of body tissue, perhaps a layer of the semi-permeable membrane used in the valve 3. This would avoid the risks of infection and/or thrombosis that can arise from something artificial being placed in the bloodstream for any length of time. The strip would also have to be hermetically sealed in plastic or a similar substance to protect it from corrosion.

When 4 comes close enough to 5 it activates the reed switch and completes a circuit from the battery 6 to the switch 7. The latter then turns off the insulin pump 8. The latter is a conventional insulin pump, which is directly powered by the battery unless it is turned off. When the circuit leading to 7 is broken, therefore, the switch is deactivated and 8 resumes pumping insulin again.

The insulin syringe 9 and pump housing 10 must be made of a plastic or other material that would not break after a heavy impact. This is important, as the sudden release of large amounts of insulin following an accident, for example, would clearly be dangerous.

When the insulin reaches a certain level, an early warning system indicates that this needs to be replenished. This system is activated by two metal contacts 11 within the body of either side of the syringe 9. As the piston 12 is metallic, a circuit is completed when it reaches the contacts 11. This then activates an alarm 13, to produce both a vibrating and an audible low-insulin warning to the patient. To avoid the alarm going off at inconvenient times, the insulin can be topped up beforehand as described below.

As the pump continues to function, this circuit is broken and the alarm is switched off when the piston 12 passes the contacts 11. When all of the insulin is used up, however, another circuit is completed when the piston reaches the contacts 14. This activates the switch 15 to turn off the pump 8. The pump can only then be restarted by refilling the insulin though the skin 16 via a self-sealing septum 17. The latter could perhaps be made of the kind of latex used to seal vials of insulin.

The insulin pump case 10 would be located in the subcutaneous fat just below the skin. It would have to be held in place in some way, e.g. with permanent sutures or stitches to prevent the reed switch from becoming detached and to ensure that the entry to the septum 17 could be easily located. A small but permanent mark on the outside of the skin would also be needed to identify the centre of the septum 17 for injection purposes.

The funnel shaped section 18 that leads from the septum would have to be of strong enough material to prevent a syringe from piercing it, as this would allow insulin to enter into the body of the pump and damage the pump mechanism.

From the funnel 18 the insulin would travel down two tubes, 19 and 20, the second of which would close the exit from the syringe to prevent insulin from escaping. Refilling the insulin would then push back the piston 12 to beyond the contact point 11, so that the insulin pump could resume, assuming it was not switched off by 7 due to a low BSL.

The second tube 20 would close the exit route from the syringe in the manner shown in FIGS. 3 and 4. When insulin is injected, it descends into tubes 19 and 20. The pressure of the insulin then pushes the end of the tube 20 down, thereby preventing insulin from escaping from tube 21.

The end of tube 20 could be made of an elasticated material, which was distended by the pressure of the insulin. Alternatively, it could contain an extendable sleeve, which was spring loaded to ensure it resumed its position once the refilling process was completed.

FIG. 5

This is identical to FIG. 1, except that in addition to the insulin pump A, there is also a glucagon pump B. For diagrammatic purposes only, these are shown on top of one another. However, they would need to lie side by side, so that the two septa 17 would both be near to the surface of the skin.

To ensure that the BSL rises as quickly as possible, when the valve 3 expands this switches off the insulin pump at A 8, and simultaneously turns on the glucagon pump via the switch at B 7, using the power from the battery B 6.

One further difference between the two pumps is that the low insulin and low glucagon warnings would have to emit different sounds, so these could be clearly differentiated. One could perhaps be an intermittent and the other a continuous signal.

One risk associated with the dual pump system would be the possibility of human error, which could result in insulin and/or glucagon being injected into the wrong pumps. This would be particularly dangerous if insulin were placed into the glucagon pump, as this would mean that insulin was secreted even when the blood sugar level was low.

To safeguard against this, the external marks indicating the centre of the two septa could be clearly differentiated. In addition, the septa could be overlain with a different plastic template to match different shapes at the end of the insulin and glucagon syringes. These could act as a kind of lock and key mechanism to prevent insulin and glucagon from being deposited into the wrong pumps.

The invention claimed is:

1. A device for controlling the blood sugar level, comprising—
   (a) an intravenous valve constructed from human tissue and consisting of a semi-permeable membrane containing a glucose solution; and
   (b) a magnetic strip attached to intravenous valve for activating a reed switch;
   (c) an insulin pump that is activated and deactivated by changes in the size of the valve, which are driven by osmosis, and subsequent movement of the attached magnetic strip.

2. The device of claim 1, wherein the valve controls two pumps, which deliver insulin and glucagon alternately in response to changes in the blood sugar level.

* * * * *